United States Patent [19]

Klein et al.

[11] Patent Number: 5,958,774

[45] Date of Patent: Sep. 28, 1999

[54] METHOD FOR GENE TRANSFER INTO CELLS ACTIVATED FROM A QUIESCENT STATE

[75] Inventors: Antoinette Klein; Jacques Hatzfeld, both of Antony, France

[73] Assignee: Centre National de la Recherche Scientifique, Paris, France

[21] Appl. No.: 08/860,299

[22] PCT Filed: Dec. 18, 1995

[86] PCT No.: PCT/FR95/01691

§ 371 Date: Jul. 10, 1997

§ 102(e) Date: Jul. 10, 1997

[87] PCT Pub. No.: WO96/19567

PCT Pub. Date: Jun. 27, 1996

[30] Foreign Application Priority Data

Dec. 22, 1994 [FR] France ................................. 94 15497

[51] Int. Cl.⁶ .............................. C12N 15/12; C12N 5/10; C07K 16/24; C07H 21/04

[52] U.S. Cl. ......................... 435/455; 435/456; 435/325; 435/372; 435/373; 435/384; 435/385; 435/386; 435/405; 435/320.1; 530/350; 530/387.1; 530/388.23; 536/24.5

[58] Field of Search ................................ 435/325, 172.3, 435/320.1, 373, 377, 384, 385, 386, 405, 455, 456, 372; 530/388.23, 350, 387.1; 536/24.5

[56] References Cited

FOREIGN PATENT DOCUMENTS

WO 92/11355 7/1992 WIPO.
WO 93/25216 12/1993 WIPO.

OTHER PUBLICATIONS

By A. Hatzfeld et al., "Increased Stable Retroviral Gene Transfer in Early Hematopoietic Progenitors Released from Quienscence", *Human Gene Therapy*, vol. 7, No. 2, Jan. 20, 1996, pp. 207–213.

By P. Sansilvestri et al., "Early CD34$^{high}$ Cells Can be Separated into KIT$^{high}$ Cells in Which Transforming Growth Factor–β (TGF–β) Downmodulates c–kit and KIT$^{low}$ Cells in Which Anti–TGF–β Upmodulates c–kit", *Blood*, vol. 86, No. 5, Sep. 1, 1995, pp. 1729–1735.

By Olivier Danos et al., "Safe and efficient generation of recombinant retroviruses with amphotropic and ecotropic host ranges", *Proceedings of the National Academy of Sciences*, vol. 85, No. 17, Sep. 1988, pp. 6460–6464.

By R. K. Strair et al., "Retroviral mediated gene transfer into bone marrow progenitor cells: use of beta–galactosi–dase as a selectable marker", *Nucleic Acids Research*, vol. 18, No. 16, Aug. 25, 1990, pp. 4759–4762.

By N. Ferry et al., "Retroviral–mediated gene transfer into hepatocytes in vivo" *Proceedings of the National Academy of Sciences*, vol. 88, No. 19, Oct. 1, 1991, pp. 8377–8381.

J.M. Hows et al., "Growth of human umbilical–cord blood in longterm haemopoetic cultures", *The Lancet*, vo. 340, No. 8810, Jul. 4, 1992, pp. 73–76.

By J. Hatzfeld et al., "Release of Early Human Hematopoietic Progenitors from Quiescence by Antisense Transforming Growth Factor β1 or Rb Oligonucleotides", *The Journal of Experimental Medicine*, vol. 174, Oct. 1991, 925–929.

By J. Hatzfeld et al., "Antisense oligonucleotides for inhibitors and tumor suppressor genes reveal the hemato–poietic potential of quiescent progenitors", *The Negative Regulation of Hematopoiesis*, vol. 229, 1993, pp. 283–289.

By L. Lu et al., "High Efficiency Retroviral Mediated Gene Transduction into Single Isolated Immature and Replatable CD34$^{3+}$Hematopoietic Stem/Progenitor Cells from Human Umbilical Cord Blood", *The Journal of Experimental Medicine*, vol. 178, No. 6, Dec. 1, 1993, pp. 2089–2096.

By T. Moritz et al., "Human Cord Blood Cells as Targets for Gene Transfer: Potential Use in Genetic Therapies of Severe Combined Immunodeficiency Disease", *The Journal of Experimental Medicine*, vol. 178, Aug. 1993, pp. 529–536.

By J. Hatzfeld et al., "Purification and Release from Quiescence of Umbilical Cord Blood Early Progenitors Reveal Their Potential to Engraft Adults", *Blood Cells*, 1994, pp. 430–435.

By Ma–Lin Li et al., "Additive Effects of Steel Factor and Antisense TGF–β1 Oligodeoxynucleotide on CD34$^+$Hematopoi–etic Progenitor Cells", *Leukemia*, vol. 8, No. 3, Mar. 1994, pp. 441–445.

BY A.A. Cardoso et al., "Release from quiescence of CD34$^+$CD38$^-$human umbilical cord blood cells reveals their potentially to engraft adults", *Proceedings of the Na–tional Academy of Sciences*, vol. 90, No. 18, Sep. 15, 1993, pp. 8707–8711.

By A. Hatzfeld et al., "Release from Quiescence of the Human Hematopoietic Stem Cell Compartment", *British Jour–nal of Haematology*, vol. 87, Supplement 1, 1994, p. 97.

By A. Hatzfeld et al., Release from Quiescence of the Human Hematopoietic Stem Cell Compartment: Application in Early Progenitor Amplification and High Efficiency Gene Transfer, *Blood –The Journal of The American Society of Hematology*, vol. 84, No. 10, Suppl. 1, Nov. 15, 1994, p. 126a.

By A. Hatzfeld et al., "Large Scale Gene Transfer in Early Human Hematopoietic Progenitors", *Journal of Cellular Biochemistry*, 1993, p. 249.

*Primary Examiner*—David Saunders
*Assistant Examiner*—F. Pierre VanderVegt
*Attorney, Agent, or Firm*—Young & Thompson

[57] ABSTRACT

A method is disclosed for gene transfer into a culture of primitive stem cells which comprises a prestimulation step of adding a blocking agent to block at least one inhibitor of a cell cycle of said primitive stem cells. The prestimulation is time-limited for a period of less than approximately 36 hours so that said culture of primitive stem cells retains hematopoietic potential.

25 Claims, 2 Drawing Sheets

METHOD FOR GENE TRANSFER INTO CELLS ACTIVATED FROM A QUIESCENT STATE

BACKGROUND OF THE INVENTION

Generally, the invention relates to a method for gene transfer into cells activated from a quiescent state, in particular hematopoietic stem cells, and the cells thus obtained.

DESCRIPTION OF THE RELATED ART

Progress in the identification and cloning of genes that are responsible for human genetic diseases has led to a major program for the improvement of gene transfer technology (Anderson, W. F. (1992) Science, 256: 808–813; Miller, A. D. (1992) Nature, 357: 455–460; Morgan, R. A., & Anderson, W. F. (1993) Annu. Rev. Biochem., 62: 191–217; Karilsson, S. (1991) Blood, 78: 2481–2492). For example, different viral vectors have been used for hematopoietic stem cells, each having their own advantage (Anderson, W. F. (1992), mentioned above). The insertion of a retroviral vector into the host genome ensures its replication in the host cell. This insertion requires an active proliferative state (Anderson, W. F. (1992), mentioned above; Varmus, H. E., Padgett, T., Heasley, S., Simon, G., & Bishop, J. M. (1977), Cell., 11: 307–319; Nolta, J. A., & Kohn, D. B. (1990) Hum. Gene Ther., 1: 257–268; Miller, D. G., Adam, M. A., & Miller, A. D. (1990) Mol. Cell. Biol., 10: 4239–4242) which does not exist in the compartment of the hematopoietic stem cell which is in a quiescent state (Lajtha, L. G., & Schofield, R. (1974) Differenciation, 2: 313–320), or in other types of stem cells and somatic cells such as the hepatic cells. Using antisense oligonucleotides against inhibitor gene, in particular TGF-β-1, has shown that the early progenitors of human bone marrow can be released from their quiescent state by blockage of an autocrine TGF-β (Hatzfeld, J., Li, M.-L., Brown, E. L., Sookdeo, H., Levesque, J.-P., O'Toole, T., Gurney, C., Clark, S. C., and Hatzfeld, A. (1991), J. Exp. Med., 174: 925–929).

Moreover, where transplants of hematopoietic tissue are concerned, in the past, the capacity for transplanting samples of bone marrow has been analysed by estimating the quantity of CFU-GM (colony-forming unit—granulocyte/macrophage: granulo-monocytic progenitor) cells. However, these cells which probably play an important part in cell generation for a short period following the transplantation of a graft may not reflect the quantity of more primitive cells, and in particular of hematopoietic stem cells which are important in long-term hematopoiesis. The stem cells involved in long-term transplants represent a small sub-population of cells which may possibly have the phenotype CD34+CD38− (compartment of the hematopoietic stem cell: cells rich in membrane antigen CD34 and poor in maturation membrane antigen CD38).

Recently, human cord blood has proved to be sufficient for reconstituting hematopoiesis after transplantation in children (Gluckman, E., Broxmeyer, H. E., Auerbach, A. D., Friedman, H. S., Douglas, G. W., Devergie, A., Esperou, H., Thierry, D., Socie, G., Lehn, P., Cooper, S., English, D., Kurtzberg, J., Bard, J., & Boyse, E. A. (1989), N. Eng. J. Med., 3: 1174–1178; Broxmeyer, H. E., Douglas, G. W., Hangoe, G., Cooper, S., Bard, J., English, D., Arny, M., Thomas, L., & Boyse, E. A. (1989) Proc. Natl. Acad. Sci. USA, 86: 3828–3832; Broxmeyer, H. E., Hangoe, G., & Cooper, S. (1992) Bone Marrow Transplant., 9: 7–10). In vitro, the data from various laboratories (Broxmeyer, H. E., Hangoe, G., Cooper, S., Ribeiro, R. C., Graves, V., Yoder, M., Wagner, J., Vadhan-Raj, S., Benninger, L., Rubinstein, P., & Broun, E. R. (1992) Proc. Natl. Acad. Sci. USA, 89: 4109–4113; Lu, L., Xiao, M., Shen, R.-N., Grisby, S., & Broxmeyer, H. E. (1993) Blood, 81: 41–48; Hows, J. M., Bradley, B. A., Marsh, J. C. W., Luft, T., Coutinho, L., Testa, N. G., & Dexter, T. M. (1992) Lancet, 340: 73–76; Cardoso, A. A., Li, M. L., Batard, P., Hatzfeld, A., Brown, E. L., Levesque, J.-P., Sookdeo, H., Panterne, B., Sansilvestri, P., Clark, S. C., & Hatzfeld, J. (1993) Proc. Natl. Acad. Sci. USA, 90: 8707–8711, suggesting that cord blood has a greater capacity for generating progenitors in culture than that of bone marrow, and consequently that cord blood could be suf ficient to effect transplants of hematopoietic tissues onto adult recipients.

However, a rapid gene transfer into the whole (totality) of the compartment of the hematopoietic stem cell or of any other stem or somatic cell at rest (this state of rest also being called "quiescence" or as corresponding to the Go phase), has not been satisfactorily achieved to date.

SUMMARY OF THE INVENTION

Gene transfer into cells activated from a quiescent state, in particular hematopoietic stem cells activated from a quiescent state, is one of the aspects of the invention.

The subject-matter of the invention is also quiescent cells, in particular quiescent hematopoietic stem cells, containing a heterologous gene.

The subject matter of the invention is also hematopoietic tissue containing a heterologous gene likely to form long-term grafts.

The invention relates to cells, in particular hematopoietic stem cells, containing in their genome all or part of a heterologous gene.

An object of the invention relates to the use for means for blocking at least one inhibitor of the cell cycle for a period not exceeding 72 h (h: hours), and preferably not exceeding 36 h, and in particular less than 20 h, and preferably approximately 1 to 15 h, and preferably approximately 1 to 10 h, in a culture of stem cells, in order to release the stem cells from their quiescent state.

According to an advantageous embodiment, an object of the invention is the use of means for blocking at least one inhibitor of the cell cycle in a test comparing, on the one hand, a culture of stem cells in a medium which contains the aforementioned means for blocking at least one inhibitor of the cell cycle and, on the other hand, the same culture of stem cells as that mentioned above in a medium which does not contain the aforementioned means for blocking at least one inhibitor of the cell cycle, in order to determine the degree of maturity of the aforementioned stem cells.

According to another embodiment, an object of the invention is the use of means for blocking at least one inhibitor of the cell cycle in a culture of stem cells, in order to release the stem cells from their quiescent state, followed by a step in which genes are transferred into the aforementioned stem cells.

Within the framework of the invention, the stem cells are advantageously hematopoietic cells and the means for blocking at least one inhibitor of the cell cycle advantageously comprises anti-TGF-β.

Another object of the invention relates to cells, in particular hematopoietic stem cells, containing all or part of a heterologous gene in their genome, which are likely to be obtained according to the method comprising the following steps:

the preatimulation of quiescent cells, in particular of quiescent hematopoietic stem cells, in a medium containing:

direct or indirect means for blocking at least one inhibitor of the cell cycle of the said cells, in particular of the said hematopoietic stem cells, for a period which is sufficient to release the cells, in particular the hematopoietic stem cells, from their quiescent state, and preferably does not exceed 72 h, and preferably does not exceed 36 h, and is in particular less than approximately 20 h, and is preferably approximately 1 to 15 h, and preferably approximately 1 to 10 h, and substances, in particular cytokines, for permitting the activation of a cell cycle and/or subsequently the passage of at least one cell cycle, the step comprising transfer by contacting the cells, in particular the hematopoietic stem cells, obtained in the previous step, with all or part of a heterologous gene, in a medium permitting the transfer of all or part of the heterologous gene into the genome of the cells, in particular of the hematopoietic stem cells, in order to obtain cells, in particular hematopoietic stem cells, including all or part of a heterologous gene, and the possible recovery of the cells, in particular of the hematopoietic stem cells, obtained in the previous step.

Yet another object of the invention relates more particularly to hematopoietic Stem cells containing in their genome all or part of a heterologous gene and having an in vitro multiplication potential equal to or greater than $10^6$ and a differentiation potential likely to cover all hematopoietic lineages.

Hematopoietic stem cells are defined as quiescent cells which can give rise to all hematopoietic lineages and to the cells deriving therefrom. Whatever the origin of the stem cells (fetal liver, fetal marrow, cord blood, adult marrow, peripheral blood), their proliferation potential is always very high: one cell giving rise to more than 1 to $20\times10^6$ cells in vitro. This number can be higher if new cytokines and bioreactors are used.

The hematopoietic stem cells can come from samples of bone marrow originating in a puncture of the iliac crest on bone marrow donors.

Hematopoietic stem cells can also be recovered from cord blood taken immediately after birth, from fetal liver or marrow, from peripheral blood or from any other organ of the hematopoietic system.

A multiplication potential equal to or greater than $10^6$ means that a single hematopoietic stem cell can give rise, under suitable conditions, to $10^6$ blood cells.

The multiplication potential of the hematopoietic stem cells of the invention can reach 1 to $20\times10^6$ cells in Stem GEM* medium and in traditional culture. This figure can be higher if new cytokines and bioreactors are used.

Hematopoietic lineages is the term used to describe all of the cells giving rise to one of the different blood cell types.

Quiescent cells likely to be within the framework of the invention is the term used to describe cells which do not multiply in an ordinary physiological situation and are likely to be activated in culture. Examples that can be cited are: cells of the liver, cells of the bony tissue, endothelial cells, cells of the tissue of the nervous system, etc. . . . , or hematopoietic stem cells, the majority of which remain quiescent in the normal individual.

According to an advantageous embodiment, the invention relates to cells, in particular hematopoietic stem cells, including, inside themselves or on their surface, means of blocking any inhibitor of their cell cycle.

The following can be cited as means of blocking inhibitors of the cell cycle inside the cell: antisense oligonucleotides, ribozymes, natural or synthetic chemical inhibitors, blocking antibodies, cytokines such as TNF, interferons or factors such as MIP-1, platelet factor 4 or FGF. These can penetrate naturally with suitable culture media or by electroporation, by microinjection or by any other method using a transport through the membrane such as liposomes.

The following can be cited as blocking means inhibiting the cell cycle on the surface of the cell: antibodies of receptors or of membrane antigens, receptor ligands, natural or synthetic, combinations of cytokines comprising various interleukins and CSFs (colony-stimulating factors) or hematopoietic growth factors.

Antibodies and ligands affix themselves specifically to an antigen or a receptor which corresponds to them.

In the cells of the invention, in particular in the hematopoietic stem cells, the blocking means can consist in those chosen from among: anti-inhibitors of the cell cycle, for example agents blocking tumor-suppressing genes, antagonists of TGF-β such as: antisense oligonucleotides of TGF-β, antibodies neutralizing TGF-β, soluble receptors of TGF-β or natural or synthetic inhibitors of TGF-β.

The abbreviation TCF-β corresponds to a "transforming growth factor" and corresponds to a family of proteins.

Examples that can be cited of tumor-suppressing antigens are pRb, p107 (Zhu et al., Genes and development, 7: 1111–1125, 1993), p130 (Hannon et al., Genes Dev., 7: 23–2391, 1993), p300, p53, p15 (Hannon G. J. & Beach D. (1994): "p15$^{INK4B}$ is a potential effector of TGF-β-induced cell cycle arrest", Nature, 371: 257), p16 (Ivison A. J. (1994): "p16 and familial melanoma", Nature Genet., 371: 180, Sansilvestri P. Doctoral Thesis Paris XI, 1994), p21 (Xiong Y., et al., & Beach D. (1993): "p21 is a universal inhibitor of cyclin kinases", Nature, 396: 701), and p27 (Polyak et al. (1994a): Cloning of p27$^{kiP1}$, a cyclindependent kinase inhibitor and a potential mediator of extracellular antimitogenic signals", Cell. 78: 59–66; Polyak et al. (1994a): p27$^{kip1}$, a cyclin-cdk inhibitor, links transforming growth factor b and contact inhibition to cell cycle arrest", Genes Development, 8: 9–22).

The term antagonists of TGF-β is used to describe an agent which neutralizes in vitro or in vivo the biological activity of TGF-⊕, types 1, 2 or 3.

The term neutralizing antibodies is used to describe an antibody or a combination of antibodies, preferably a monoclonal antibody or a combination of monoclonal antibodies, which neutralizes in vitro or in vivo the biological activity of TGF-β of types 1, 2 or 3.

The term natural or synthetic inhibitor of TGF-β is used to describe a substance which inhibits in vitro or in vivo the biological activity of TGF-β.

5'-CCCGGAGGGCGGCATGGGGGA-3' (SEQ ID NO: 1) can be used advantageously as an antisense nucleotide of TGF-β (J. Hatzfeld et al., "Release of Early Human Hematopoietic Progenitors from Quiescence by Antisense Transforming Growth Factor β1 or Rb Oligonucleotides", J. Exp. Med., vol. 174, October 1991, pp. 925–929).

Also conceivable as blocking means are a cytokine or a combination of cytokines likely to release the stem cells from the quiescent state for a period of less than approximately 10 h.

The following can be cited as cytokines: all interleukins, all CSFs (colony stimulating factors), all immunomodulators including the following interleukins: IL1, IL2, IL3, IL4, IL5, IL6, IL7, IL8, TL9, IL10, IL11, IL12, IL13, TNFs (tumor necrosis factors), interferons, LIFs (leukemia inhibiting factors), MIP-1 (inflammatory protein produced or acting on the macrophage, Dunlop D. J. et al.: Blood, 1992, 79: 2221–2225), the Steel factor, and the ligand of the receptor flt-3 or FL.

A combination of cytokines that can be cited is IL3, IL6, GMCSF (growth factor of granulo-monocytic progenitors), SF and FL.

The means of blocking any inhibitor of the cell cycle must be used in a quantity suitable for neutralizing the activity of any inhibitor of the cell cycle. They are generally used in concentrations ranging from 0.1 to 1000 units/ml, preferably from 1 to 10 units/ml.

When an antisense oligonucleotide of TGF-β is used, this can be used at from 0.03 $\mu$M to 100 $\mu$M, in particular from 5 $\mu$M to 8 $\mu$M, or from 0.01 $\mu$M to 0.5 $\mu$M in the presence of certain agents for example lipid agents permitting a better penetration of the oligonucleotides into the cell than the previously described penetrations.

According to an advantageous embodiment, the invention relates to quiescent cells, in particular hematopoietic stem cells containing, integrated into their genome, all or part of a heterologous gene.

In fact, after the transfer of all or part of a heterologous gene into their genetic patrimony, the cells can be returned to the quiescent state.

The method of the invention according to which, after the transfer of all or part tf a heterologous gene, the cells are returned to the quiescent state, is detailed later in the present description.

The invention also relates to a composition of hematopoietic cells or a cluster of hematopoietic cells or a tissue of hematopoietic cells which are likely to maintain a continuous hematopoiesis for a period greater than or equal to approximately 6 months, and consist in hematopoietic stem cells and where appropriate of progenitors in the course of differentiation, the aforementioned stem cells and the aforementioned progenitors containing all or part of a heterologous gene.

The expression "maintaining a continuous hematopoiesis" corresponds to a physiological production of mature blood cells.

The invention also relates to a method of transferring all or part of a heterologous gene into the genome of cells activated from a quiescent state, in particular of hematopoietic stem cells activated from a quiescent state, characterized in that it comprises the following steps:

the prestimulation of quiescent cells, in particular of quiescent hematopoietic stem cells, in a prestimulation medium containing:

direct or indirect means for blocking at least one inhibitor of the cell cycle of the said quiescent cells, in particular of the said hematopoietic stem cells, for a period which is sufficient to release the cells, in particular the hematopoietic stem cells, from their quiescent state, and preferably does not exceed approximately 72 h, preferably does not exceed 36 h, and is in particular less than approximately 20 h and is preferably approximately 1 to 15, and preferably approximately 1 to 10 h and:

substances, in particular cytokines, for permitting the activation of a cell cycle and/or subsequently the passage of at least one cell cycle of the said cells, in particular of the said stem cells, the step comprising transfer by contacting the cells, in particular of the prestimulated hematopoietic stem cells obtained in the previous step, with all or part of a heterologous gene in a medium permitting the transfer of all or part of the heterologous gene into the genome of the cells, in particular of the hematopoietic stem cells, in order to obtain cells, in particular hematopoietic stem cells including all or part of a heterologous gene, the possible recovery of the cells, in particular of the hematopoietic stem cells, obtained in the previous step.

The quiescent hematopoietic stem cells used within the framework of the gene transfer can be obtained from fetal hematopoietic organs, from cord blood, from bone marrow, from peripheral blood or from any other hematopoietic organ, according to the method described in the examples (Hatzfeld J., Batard P., Cardoso A. A., Li M.-L., and Hatzfeld, A.: "Purification and in vitro assay of early human hematopoietic progenitors", 205–221, in Culture of Hematopoietic Cells, Freshney R. I., Pragnell I. B., Freshney M. G., 1994).

As far as the period of prestimulation is concerned, it does not exceed approximately 72 h, preferably 36 h, and is preferably approximately 1 to 15 h, and preferably approximately 1 to 10 h.

The induction of the prestimulation can take place for an extremely short time, of the order of some seconds, but the triggering of all of the cell mechaniams permitting the stem cell to leave the Go phase takes at least an hour.

In the case of the use of anti-TGF-β as a blocking means, prestimulation does not exceed approximately 72 h, since beyond 72 h, and in particular beyond 19 h, there is no supplementary effect beyond the prestimulation obtained with combinations of cytokines or anti-TGF-β and combinations of cytokines.

The expression "activation of a cell cycle" corresponds to the introduction of functions permitting the passage of the cell cycle.

The expression "the passage of at least one cell cycle" corresponds to a division of the genome (S phase), and to a mitosis giving two identical cells.

At the end of the gene transfer, the cells can either multiply and differentiate, or they can be returned to the quiescent state, as is explained later in the description.

When the transfected stem cells are returned to the quiescent state, the compartment of the stem cell has "aged" by one division, which is not much compared with its enormous hematopoietic potential.

In the method of the invention, according to an advantageous embodiment the prestimulation medium comprises: IMDM (Iscove Dubelcco Modified Medium), StemGEM* (corresponding to a range of media marketed by the C.N.R.S.), cytokines, antagonists of TGF-β such as antisense oligonucleotides of TGF-β, antibodies neutralizing TGF-β, soluble receptors of TGF-β or natural or synthetic inhibitors of TGF-β, combinations of cytokins likely to block in a short time space (less than 72 h, preferably less than 10 h) the inhibitors of the cell cycle of the quiescent stem cells, controlled or not by TGF-β.

According to an embodiment of the method of the invention, the cytokins are chosen from among a combination of at least four cytokines chosen from among the following cytokines: IL1 (interleukin 1), IL2 (interleukin 2), IL3 (interleukin 3), IL4 (interleukin 4), IL5 (interleukin 5), IL6 (interleukin 6), IL7 (interleukin 7), IL11 (interleukin 11), GM-CSF (granulocyte-macrophage colony-stimulating factor; growth factor of granulo-monocytic progenitors), G-CSF (granulocyte colony-stimulating factor; growth factor of granulocytic progenitors), Steel factor (SF), ligand of the receptor FLT3 (FL), erythropoietin, TNF, LIF (leukemia inhibiting factor), thrombopoietin, insulins and FGF.

The transfer of all or part of a heterologous gene can take place with a coculture of cells, in particular of hematopoietic stem cells, which have been prestimulated according to the first step of the method of the invention, and cells producing a vector, such as a viral vector or a retrovirus, containing all or part of the gene to be transferred (Ferry N., Duplessis O., Housain D., Danos O., and Heard J.-M. "Retroviral-mediated gene transfer into hepatocytes in vivo". Proc. Natl. Acad. Sci., USA, 88: 8377–8381, 1991).

The transfer can also be carried out by contacting the cells, in particular of the prestimulated hematopoietic stem cells, with the supernatant of cells containing a vector, such as a viral vector or a retrovirus including all or part of the gene to be transferred (Lu, R. L., Xiao, M., Clapp, D.-W., Li. Z.-H., & Broxmeyer, H. E (1993), J. Exp. Med., 178: 2089–2096).

The invention also relates to a method of transferring all or part of a heterologous gene into the genome of cells activated from a quiescent state, in particular of hematopoietic stem cells activated from a quiescent state, characterized in that it comprises the following steps:

the prestimulation of quiescent cells, in particular of quiescent hematopoietic stem cells, in. a prestimulation medium containing:

direct or indirect means for blocking at least one inhibitor of the cell cycle of the said cells, in particular of the hematopoietic stem cells, for a period which is sufficient to release the cells, in particular the hematopoietic stem cells, from their quiescent state, and preferably does not exceed approximately 72 h, and preferably does not exceed approximately 36 h, and is in particular less than approximately 20 h and is preferably approximately 1 to 15 h, and preferably approximately 1 to 10 h, and substances, in particular cytokines, for permitting the activation of a cell cycle and/or subsequently the passage of at least one cell cycle of the said cells, in particular of the said hematopoietic stem cells, the step comprising transfer by contacting the cells, in particular of the prestimulated hematopoietic stem cells obtained in the previous step, with all or part of a heterologous gene, in a medium permitting the transfer of all or part of the heterologous gene into the genome of the stem cells, by coculture of cells, in particular of prestimulated hematopoietic stem cells as indicated above and of cells producing a viral vector or a retrovirus containing all or part of the gene to be transferred, in order to obtain cells, in particular hematopoietic stem cells including all or part of a heterologous gene, and the possible recovery of the cells, in particular of the hematopoietic stem cells obtained in the previous step.

The coculture can be carried out as described in Human Cord Blood Cells as Targets for Gene Transfer: Potential Use in Genetic Therapies of Severe Combined Immunodeficiency Disease. Moritz T., Keller D. C. and Williams D. A., J. Exp. Med., 178: 529–536 (1993).

The invention also relates to a method of transferring all or part of a heterologous gene into the genome of cells activated from a quiescent state, in particular of hematopoietic stem cells activated from a quiescent state, characterized in that it comprises the following steps:

the prestimulation of quiescent cells, in particular of quiescent hematopoietic stem cells, in a prestimulation medium containing:

direct or indirect means for blocking at least one inhibitor of the cell cycle of the said cells, in particular of the said hematopoietic stem cells, for a period which is sufficient to release the cells, in particular the hematopoietic stem cells, from their quiescent state, and preferably does not exceed approximately 72 h, and preferably does not exceed approximately 36 h, and is in particular less than approximately 20 h and is preferably approximately 1 to 15 h, and preferably approximately 1 to 10 h, and substances, in particular cytokines, for permitting the activation of a cell cycle and/or subsequently the passage of at least one cell cycle of the said stem cells, the step comprising transfer by contacting the cells, in particular of the prestimulated hematopoietic stem cells obtained in the previous step, with all or part of a heterologous gene, in a medium permitting the transfer of all or part of the heterologous gene into the genome of the cells, in particular of the hematopoietic stem cells, by contacting the cells, in particular the stem cells prestimulated as indicated above with supernatant of cells containing a vector, such as a viral vector or a retrovirus containing all or part of the gene to be transferred, in order to obtain cells, in particular stem cells including all or part of a heterologous gene, and the possible recovery of the cells, in particular of the stem cells obtained in the previous step.

The invention also relates to a method of transferring all or part of a heterologous gene into the genome of cells activated from a quiescent state, in particular of hematopoietic stem cells activated from a quiescent state, characterized in that it comprises the following steps:

the preatimulation of quiescent cells, in particular of quiescent hematopoietic stem cells, in a preatimulation medium containing:

means for blocking at least one inhibitor of the cell cycle of the said cells, in particular of the said hematopoietic stem cells, for a period which is sufficient to release the cells, in particular the hematopoietic stem cells, from their quiescent state, and preferably does not exceed approximately 72 h, and is in particular less than approximately 20 h, and is preferably approximately 1 to 15 h, and preferably approximately 1 to 10 h, and:

substances, in particular cytokines, for permitting the activation of a cell cycle and/or subsequently the passage of at least one cell cycle of the said stem cells, in particular of the said hematopoietic stem cells, the step comprising transfer by contacting the cells, in particular of the prestimulated hematopoietic stem cells obtained in the previous step, with all or part of a heterologous gene, in a medium permitting the transfer of all or part of the heterologous gene into the genome of the cells, in particular of the hematopoietic stem cells, in order to obtain cells, in particular hematopoietic stem cells, including all or part of a heterologous gene, all or part of the heterologous gene originating in particular in a vector, such as a viral vector or a retrovirus, produced by a producing culture to which has been added a viral agent, such as an anti-TGF-β, an anti-interferon or any agent permitting an increase in the production and/or the stability of the vector, and the possible recovery of the cells, in particular of the hematopoietic stem cells obtained in the previous step.

As far as the stem cells are concerned, they are possibly returned to the quiescent state after the transfer step.

According to an advantageous embodiment of the method of the invention, the medium permitting the transfer of all or part of the heterologous gene may be comprised of, or contains: DMEM (Eagle medium modified by Dubelcco), IMDM (Iscove medium modified by Dubelcco), cytokines an antagonist of TGF-β as defined above, and anti-interferons, or any other viral agent permitting an increase in the production and/or the stability of the viral vector or of the retrovirus, containing the gene to be transfected, when the transfer of all or part of the heterologous gene is carried out by coculture of the stem cells and of the viral vector, or of the retrovirus.

When the transfer is carried out using a supernatant of the culture containing the vector, the titer of the vector produced by the producer culture can advantageously be increased by adding to the culture producing the vector an anti-TGF-β or an anti-interferon or any other agent likely to increase the production and/or the stability of the vector.

The invention also relates to a method permitting an increase in the titer of a vector, such as a viral vector, or a retrovirus, which vector is produced by a producer culture, by the addition to the said culture of a viral agent such as an anti-TGF-β, an anti-interferon, or any vector-stabilizing agent.

At the end of the stage transferring all or part of the heterologous gene into the stem cells, the stem cells which include in their genome all or part of a heterologous gene can be placed in a suitable medium, in particular a liquid medium or a semi-solid medium, in order to multiply and to differentiate into differentiated hematopoietic cells, in particular into differentiated blood cells.

Examples of differentiated cells that can be cited are granulocytes, monocytes, megacaryocytes, and erythrocytes.

At the end of the stage transferring all or pare of the heterologous gene into the hematopoietic cells, a step can also be advantageously envisaged which comprises the returning to the quiescent state of the hematopoietic stem cells containing all or part of the heterologous gene, which step can be carried out with the help of at least one inhibitor of the cell cycle, such as TGF-β.

More precisely, in order to return the stem cells to the quiescent state (i.e. in Go phase) after the transfer of all or part of a heterologous gene, it is possible to proceed as follows.

The attraction of the method of the invention over all other methods lies in the fact the activation of the quiescent cell takes place in an extremely short period of time (of the order of 1 to 72 preferably 6 to 12 hours starting from the end of the prestimulation step) thanks to a synchronization of the departure from the Go phase for all the quiescent cells at the time of the prestimulation step of the method of the invention as described above. This allows the transfected cells to be returned to the Go phase, after the transfer by addition of TGF-β. This guarantees that during the gene transfer the stem cells have not lost their hematopoietic potential, inasmuch as the division number is not more than 1 or 2.

The heterologous gene of which all or part is introduced into the genome of hematopoietic stem cells can be chosen from among the following genes: markers: Neo (neomycin resistance gene), CD2 (leucocytic antigen), nls-lacZ, or genes correcting a hematopathy or any other pathology such as ADA (adenosine deaminase gene), ALDP (gene correcting adrenoleucodystrophy), TK (suicide gene allowing cells to be killed in the presence of acyclovir under the control of viral promoters), this list not being exhaustive.

Current methods of gene transfer do not allow the compartment of the stem cell to be transfected in such a way that the lymphoid lineages are satisfactorily transfected. This is important if one wishes cell therapy to be applicable to the treatment of AIDS or of pathologies affecting the B cells (cells, e.g., lymphomas). The transfer method of the invention effectively permits transfer into the B and T lineages, a fact which can be verified using the following two models which permit the development of the compartment of the stem cell to be studied:

humanized SCID mice (McCune J. M., Namikawa R., Weilbaecher K. N., Kaneshima H., Schultz L. D., Lieberman M. and Weissman I. L.: "The SCID-hu mouse: Murine model for the analysis of human hematolymphoid differentiation and function". Science, 241: 1632, 1988), and:

cultures of thymic epithelium (Plum J., De Smedt M., Defresne M.-P., Leclerq, G., and Vandekerckhove B.: "Human CD34+ fetal liver stem cells differentiate to T cells in a mouse thymic microenvironment". Blood 84: 1587–1593, 1994).

These methods permit all the lineages including B and T to be obtained in the first case, and the T lineage in the second case.

The media used to permit the division of the compartment of the stem cell once activated to leave the Go phase must respect the expression of the receptors of the stem cell according to the recommendations published in Hatzfeld A. et al., Hématol., 1993, 35: 281–283, and in Panterne et al., J. Cell. Physiol., 91, 1481–1489.

The method of the invention makes it possible in particular:

to increase the titer of a vector containing all or part of a heterologous gene to be transfected, in particular into hematopoietic stem cells, to transfer all or part of a gene into quiescent cells, in particular hematopoietic stem cells, in which such a transfer was aleatoric up until the present;

to improve the effectiveness of transfer into early hematopoietic progenitors such as CFU-GEMM, LTC-IC (long-term culture-initiating cell), HPP-Q (high proliferative potential quiescent cells) and lymphoid progenitors having a strong proliferative potential considered as "the compartment of the stem cell" compared with the transfer already carried out using the methods of the state of the art; for example, the method will permit a transfer into more than 95% of CFU-GEMMs that can develop into colonies containing more than $10^5$ cells, the Stem GEM* media distributed by the CNRS permitting the evaluation of such cells of the compartment of the stem cell, humanized SCID mice (severe combined immunodeficiency mice) and systems of stromal or thymic epithelium cultures (referred to above) permitting the evaluation of the transfer into the whole of the compartment of the stem cell; and to improve the stability of the expression during the development of the stem cells and the progenitors (amplification and differentiation), it being possible to use marker genes to track and evaluate this expression (example: nls-lacZ).

The invention also relates to a method permitting the evaluation of the maturity or immaturity of stem cells, before and/or after the transfer of genes.

More particularly, the invention relates to a method of determining the degree of maturity of stem cells, in particular hematopoietic cells, characterized in that it comprises the following steps:

a first set of stem cells, in particular hematopoietic cells, is cultured in a medium which is suitable for their culture but does not contain means for blocking at least one inhibitor of the cell cycle, for approximately 14 to approximately 28 days, preferably 18 days, a second set of stem cells, in particular hematopoietic cells, is cultured, being of the same kind and having the same degree of maturity as those mentioned above, in a suitable medium containing means for blocking at least one inhibitor of the cell cycle, these blocking means being present in the culture medium in an effective concentration (on condition that they are not diluted more than 4 times compared with the optimum concentration), for a period which does not exceed 72 h, and preferably does not exceed approximately 36 h, and is preferably approximately 1 to 15 h and more preferably from 1 to 10 h, this culture taking place for the same period as that of the first set of stem cells, and a comparison is carried out, 18 days after the culturing of each of the two sets of stem cells, of the number and type of colonies, of the difference in the totals of the colonies having a high proliferative potential (HPP-CFC=cell forming a colony having a high proliferative potential, HPP-MEG=megacaryocyte having a high proliferative potential, HPP-GEMM=granulocyte/ erythrocyte/ monocyte/megacaryocyte having a high proliferative potential) respectively between that of the second set and that of the first set corresponding to the HPP-Q colonies.

The optimum concentration of antisense oligonucleotides can be approximately 0.001 $\mu M$ to approximately 100 $\mu M$, preferably lees than approximately 10 $\mu M$.

The optimum concentration of blocking antibodies can be approximately 0.01 $\mu g/ml$ to approximately 100 $\mu g/ml$, preferably 1 $\mu g/ml$.

As far as the culture in the presence of means for blocking an inhibitor of the cell cycle is concerned, at the end of the period which does not exceed 72 h, and preferably does not exceed approximately 36 h, and which is preferably approximately 1 to 15 h and more preferably from 1 to 10 h:

either the cells can be washed in order to substantially eliminate the aforementioned blocking means, or the aforementioned blocking means can be diluted to a concentration such that they have no proliferative effect on more mature cells (i.e. progenitors which are already activated).

"Evaluation of the maturity or of the immaturity of stem cells" corresponds to the following observation.

After 18 days, the number and type of the colonies is observed under the microscope and a count is carried out of the number of mixed colonies consisting of cells of the red line and of one or more types of cells of the white line. The number of mixed colonies is higher when the cultured cell population is more immature, i.e. is comprised of younger cells some of which are quiescent. On the other hand, the more the cell which has given rise to the colony is immature, even quiescent, the greater is its proliferation potential, and thus the greater will be the size of the colony originating from this cell once activated.

This test will also be called the HPP-Q test in the following.

In order to accomplish the above, a culture of stem cells in a semi-solid or liquid medium which does not contain an anti-inhibitor of the cell cycle is compared with the same culture of stem cells in a semi-solid or liquid medium which does contain an anti-inhibitor of the cell cycle, for example anti-TGF-$\beta$.

The culture conditions in the medium which does not contain a cell cycle anti-inhibitor can use IL1, IL2, IL3, IL4, IL5, IL6, IL7, IL11, G-CSF, GM-CSF, SF, FL, FGF, insulin, erythropoietin, thrombopoietin or other cytokines which cooperate or synergize with the above.

The culture conditions in the medium which does contain an anti-inhibitor of the cell cycle for example anti-TGF-$\beta$ are as follows. Anti-TGF-$\beta$ is added in prestimulation for 10 hours in a small volume of liquid culture containing the quiescent cells such as CD34+CD38− cells (1 to 10% of the most immature CD34+s). The volume of this preculture is approximately ⅙ of the final volume. This preculture is then added to methyl cellulose with cytokines to which no anti-TGF-$\beta$ has been added, in order to arrive at the final volume.

A simplification of this procedure involves placing the anti-TGF-$\beta$ immediately in the final culture in concentrations which allow it to be active only during the first hours of the culture, preferably for the first 10 hours.

Under these conditions new colonies, larger than the previous colonies, are observed, derived from cells called high proliferative potential quiescent cells or HPP-Q cells which develop over 18 days and not just over 8, 10, 12 or 14 days as is observed without prestimulation by means of anti-TGF-$\beta$. The anti-TGF-$\beta$ thus does not need to be present for the whole period of the culture. As far as the size of colonies is concerned, this can be determined by counting under the microscope on a Mallasez slide, after sampling and dispersion of the colony in a known volume of liquid medium.

Whether the test is carried out in a liquid, clonal or non-clonal medium, the clones or the populations in the two types of culture are compared.

Where HPP-Q cells are concerned, they constitute an element of the compartment of the stem cell and, as to their phenotyping, it is a case of CD34+ kit low IL6-R low.

As far an the culture media are concerned, any medium can be used that is suitable for CFU-GEMM cells and also permits the development of the lymphoid cells.

The composition of the semi-solid culture media can be such as is described in chapter 12 of "Culture of Hematopoietic Cells, R. J. Frehsney, I. B. Pragnell, M. G. Freshney, ed. Wiley-Liss" pp. 205–221. The title of the chapter is "Purification and in vivo assay of early human hematopoietic progenitors" J. Hatzfeld, P. Batard, A. A. Cardoso, M. L. Li, A. Hatzfeld.

In accordance with the invention, the maturity or immaturity of the stem cells after the transfer of genes can be evaluated. This evaluation is carried out as indicated above, starting from the largest colonies for which it is verified, simultaneously with the aforementioned evaluation of immaturity, whether there has indeed been a transfer of genes, as indicated below in example 1.

The invention relates in particular to a method of transferring genes into the hematopoietic stem cell in which the immaturity of the stem cells is evaluated before the gene transfer, and advantageously after the transfer of genes.

This method can comprise the following steps:

1—Evaluation of the hematopoietic cells to be transplanted to ensure that they contain immature cells hereinafter called HPP-Q, an element of the compartment of the stem cell. It is in fact pointless to proceed with a transfer of genes if the cells used are not the right ones. By means of the method of evaluating the immaturity of the stem cells, a culture in a semi-solid or liquid medium, without an anti-inhibitor of the cell cycle, can be compared with the same culture in the presence of an anti-inhibitor. The difference in the number of colonies must demonstrate the appearance of new colonies, larger than the previous colonies, derived from HPP-Q cells.

2—Prestimulation of the hematopoietic cells with a medium containing an activator of the cell cycle (10 hours for an anti-TGF-β), in order to remove the hematopoietic cells from the quiescent phase, i.e., in order to activate them.

3—Transfer of genes with a viral supernatant or in coculture with cells producing viruses in a medium containing an anti-interferon and/or an anti-TGF-β.

4—After the transfer of genes, the activated hematopoietic cells should be capable of being returned to quiescence (Go phase) in a deactivation medium containing an inhibitor of this cell (TGF-β in the case of the hematopoietic stem cell).

5—Alternatively, the activated cells, whether or not they have undergone a transfer of genes, can be amplified in order to be reinjected in vivo. This can be realized with a sub-population of the cells to be reinjected in order to prevent the aplasia which generally precedes the taking up of a graft.

6—Before or after reinfusion of the cells, it is necessary to carry out a HPP-Q test, followed by an in-situ coloring or by a RT-PCR (reverse transcriptase—polymerase chain reaction) of the colonies obtained in order to evaluate the transfer of genes.

Liquid culture media such as those described in the article by Cardoso et. al. (Proc. Natl. Acad. Sci. USA, Vol. b 90,pp. 8707–8711, September 1993) can be used as prestimulation medium and before the transfer of genes.

The method of the invention also permits the assessment of the number of quiescent primitive cells (HPPQ) before the transfer of genes, in order to determine the abundance of stem cells, or after the transfer of genes, in order to determine the effectiveness of the transfer of genes into the compartment of the stem cell.

PREFERRED EMBODIMENTS OF THE INVENTOR

EXAMPLE 1

Figure 1:
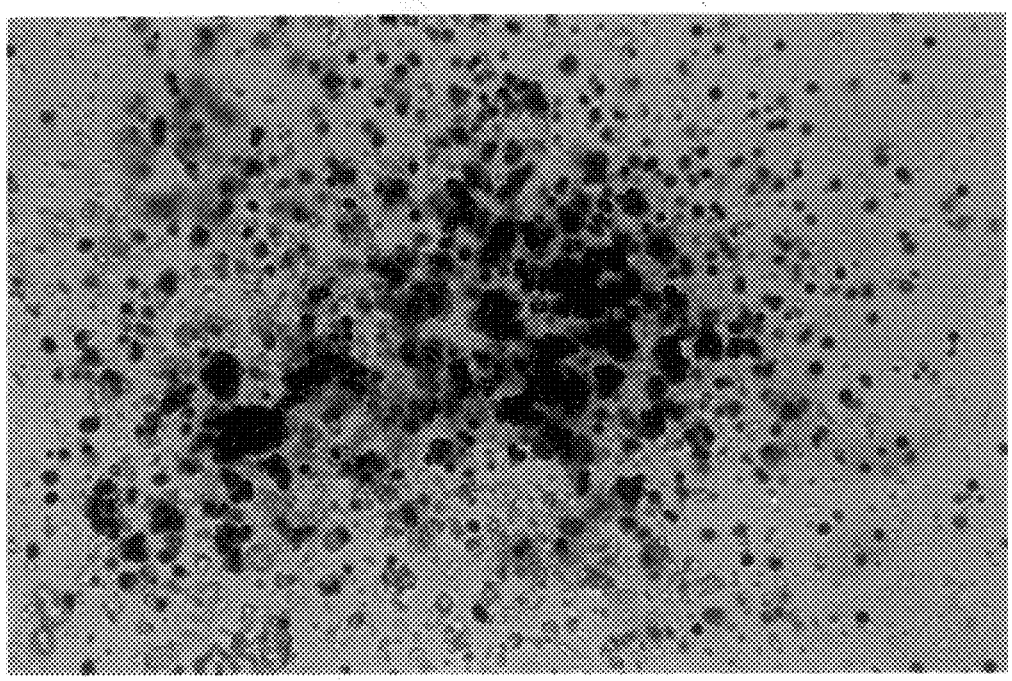
FIG. 1 represents a CPU-GEMM colony expressing in a stable manner the nls-lacZ gene demonstrated by the X-Gal coloring.

Transfer of the Nls-Lacz Gene into Hematopoietic Stem Cells

Material and Methods.
Hematopoietic growth fat antiserum

The recombinant human interleukin 3 (IL3), recombinant human interleukin 6 (IL6), recombinant human GM-CSF (granulocyte macrophage colony-stimulating factor) and recombinant human G-CSF (granulocyte colony-stimulating factor) are supplied by Genetics Institute (Cambridge, Mass.). The recombinant human erythropoietin is supplied by AMGEN (Thousand Oaks, Calif.) and the recombinant human SF (Steel factor) comes from IMMUNEX (Seattle, Wash.). The specific activities of these cytokines are respectively: $2.3 \times 10^6$ U/mg, $4 \times 10^6$ U/mg, $9.3 \times 10^6$ U/mg, $7 \times 10^4$ U/mg, $4.98 \times 10^5$ U/mg and $10^6$ U/mg. The turkey blocking antiserum, anti-TGF-β, is a gift from Dr. A. B. Roberts and M. B. Sporn (Danielpour, D., Dart, L. L., Flanders, K. C., Roberts, A. B., & Sporn, M. B. (1989) J. Cell. Physiol. 138, 79–86), of which 1 µl can neutralize 4 ng of TGF-β. It is used in a concentration of 4.2 µl/ml.

Purification of CD34+ cells

The term CD34+ cells is used to describe cells carrying the CD34 membrane antigen and including a sub-population which represents the compartment of the stem cell.

Recovery of cord blood

Samples of human cord blood are recovered from the umbilical cord/placenta immediately after birth, while the placenta remains in situ (Broxmeyer, H. E., Douglas, G. W., Hangoe, G., Cooper, S., Bard, J., English, D., Arny, M., Thomas, L., & Boyse, E. A. (1989) Proc. Natl. Acad. Sci. USA, 86, 3828–3832; Gluckman, E., Devergie, A., Thierry, D., Eperou-Bourdeau, H., Traineau, R., Gerrota, J., Brossard, Y., Van Nifterik, J., & Benbunan, M. (1992) Bone Marrow Transplant. 9, 114–117).

Purification of SBA-CD34+ cells

The mononuclear cells are obtained as described previously (Hatzfeld, J., Li, M.-L., Brown, E. L., Sookdeo, H., Levesque, J.-P., O'Toole, T., Gurney, C., Clark, S. C., & Hatzfeld, A. (1991), J. Exp. Med., 174, 925–929). Very shortly after the isolation of mononuclear cells on Ficoll Hypaque, the SBA-cells (cells not affixing themselves to soya agglutinin) are purified, eliminating the cells that have remained attached to the soya agglutinin immobilized in a covalent manner using the AIS procedure (procedure developed by the company Applied Immune Sciences). BSA CELLector Flasks are from Applied Immune Sciences Inc. Santa Clara, Calif. The positive selection of CD34+ is obtained with culture flanks covered with monoclonal CD34+ ICH3 antibodies (CD34 CELLector Flasks, AIS), washed a sufficient number of times (up to 10 times) with a Dulbecco phosphate buffered saline solution, containing 1 mM of EDTA in order to ensure the elimnination of the unattached and weakly attached cells ($CD34^{+weak}$) as observed with the reversed microscope (Hatzfeld J., Batard P., Cardoso A. A., Li M.-L., and Hatzfeld, A.: Purification and in vitro assay of early human hematopoietic progenitors, 205–221, in Culture of Hematopoietic Cells, Freshney R. I., Pragnell I. B., Freshney M. G., 1994).

This procedure routinely gives a purity of 95% (±3%) of CD34 cells. The isolated CD34+SBA- cells are then detached by a 2-hour incubation at 37° C. in iscove medium modified by Dulbecco (IMDM) to which fetal calf serum (FCS) has been added at 10% or in StemGEM* medium from the CNRS (medium without serum). The detachment of the cells must be complete, given that the cells which express a high quantity of CD34 antigens represent the most immature progenitors and are the most difficult to detach.

Composition of the media

The prestimulation and transfer media are Stem GEM* media with or without serum (CNRS National Scientific Research Centre UPR 9044 Villejuif France).

Transduction method

The line of NB16 cells, a line of cells (Danos, O., and Mulligan R. C.: "Safe and efficient generation of recombinant retroviruses with amphotropic and ecotropic host ranges". Proc. Natl. Acad. Sci., USA 85: 6460–6464, 1988) which expresses the β-galactosidase of *E. coli* (Strair, R. K., Towle, M., & Smith, B. R. (1990) Nucleic Acids Res. 18, 47–4762) is supplied by J. M. Heard and O. Danos. These cells are kept in culture in DMEM medium to which has been added 10% serum of new-born calf enriched in iron (Hyclone). This cell line produces a supernatant having a customary viral titer of 1 to $5.10^5$ units/ml. The CD34+ cells are prestimulated for various periods (50,000 CD34+ cells in 0.5 ml). They are then placed in coculture for 40 h on NB16 cells at 40% confluence in StemGEM* medium (CNRS) to which polybrene has been added at 8 μl/ml at 37° C. with 5% of $CO_2$ in a humidity-saturated atmosphere. The CD34+ cells are then gently detached, concentrated and tested for clonogenic trials.

Clonogenic trials in methyl cellulose.

The CD34+ cells are cultivated at the rate of 300–400 cells/ml according to a modification of a mixed colony test devised by Fauser and Messner (Hatzfeld, J., Li, M.-L., Brown, E. L., Sookdeo, H., Levesque, J.-P., O'Toole, T., Gurney, C., Clark, S. C., and Hatzfeld, A. (1991), J. Exp. Med., 174: 925–929; Fauser, A. A., & Messner, H. A. (1979) Blood 53, 1023). All the cultures are at least carried out in duplicate.

Coloring of the transduced colonies.

After an incubation of 14 to 21 days at 37° C. in a saturated humidified atmosphere, the colonies are counted and classified as described in an earlier manner (Zhou, Y.-Q., Stanley, E. R., Clark, S. C., Hatzfeld, J., Levesque, J.-P., Federici, C., Watt, S. M., & Hatzfeld, A. (1988) Blood 72, 1870–1874). They are then colored by the same histochemical method as that used to assess the titer of a supernatant, with X-Gal as a substrate (MacGregor, G. R., Nolan, G. P., Fiering, S., Roederer, M., & Herzenberg, L. A. (1991) Methods Mol. Biol. 7, 217–235) except for the fact that the coloring solution (1 ml/Petri dish) is twice as concentrated as for the adherent cells. The coloring reaction is carried out all night.

Statistical analysis.

The significance of differences between the treatment groups is determined using Student's t test.

Results.

The infection effectiveness of nls-lacZ depends on a 10-h period of prestimulation with anti-TGF-β.

The SBA-CD34+++ cells (most immature CD34 cells) are purified with a high recovery of cells of the compartment of the stem cell part of which is formed by the CFU-GEMMs (colony-forming units—granulocyte/erythrocyte/macrophage/megacaryocyte) having a high proliferation potential (greater than $10^5$ cells) as described in Material and Methods. These cells are preincubated for various periods with or without anti-TGF-β serum as detailed in table 1 before the coculture with NB16 cells for infection by retroviral vectors. When these cells are preatimulated for 10 h solely with cytokines and without anti-TGF-β before transduction, the transfer effectiveness increases from 1.1 to 23.8%. This increase doubles in a significant manner in the presence of anti-TGF-β serum, rising from 23.8 to 47.3%. The activation effectiveness of the anti-TGF-β disappears during preincubation times which are too long. Prestimulation periods of 20 or 48 h, or longer (not represented), with or without anti-TGF-β serum, deliver results similar to those observed after 10 h without anti-TGF-β serum.

Effect of anti-TGF-β on the transfer effectiveness of nls-lacZ in the different types of progenitors.

Figure 2:
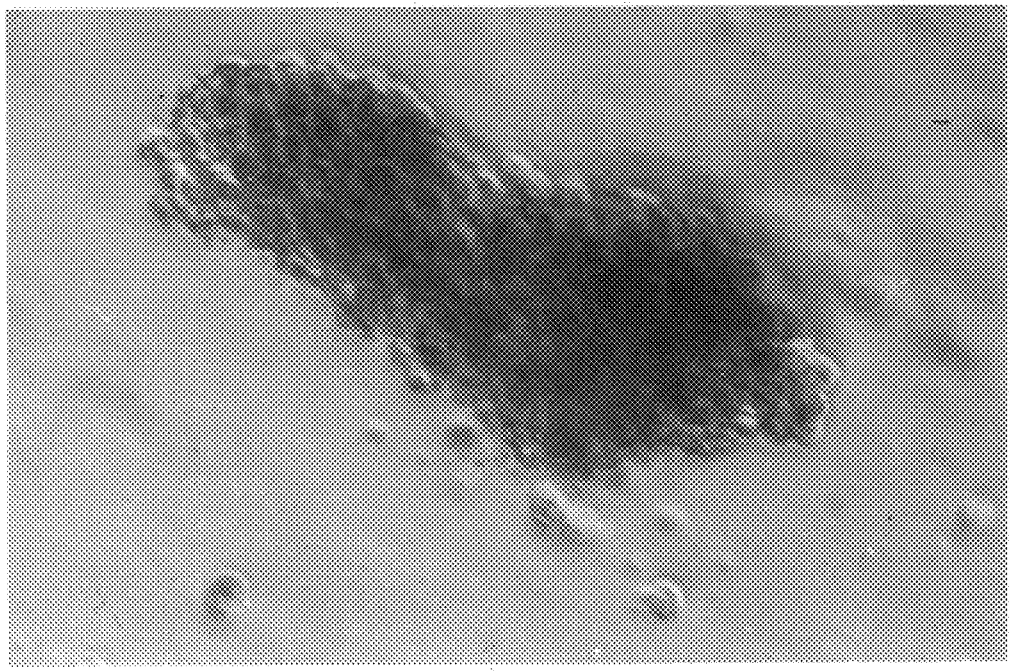
FIG. 2 represents, in a greater magnification, a group of erythroid cells of the CFU-GEMM colony with an expression of the homogeneous nls-lacZ gene in all the cells.
Figure 3:
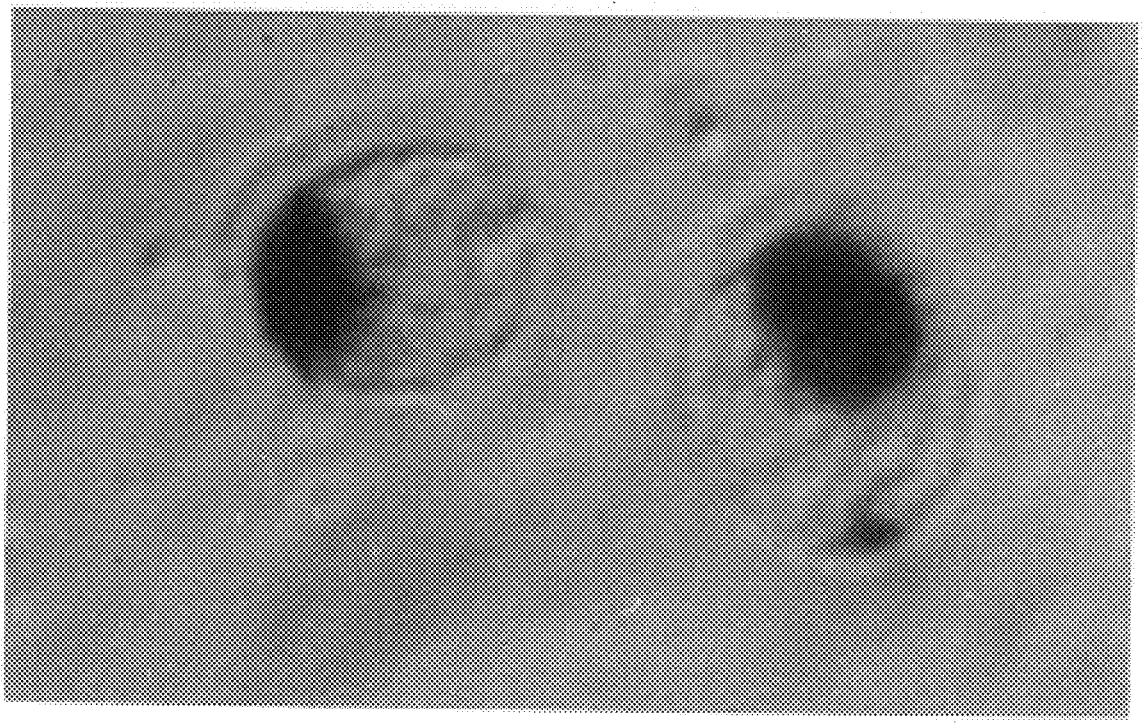
FIG. 3 shows the nuclear localization of the β-galactosidase in the macrophages and the absence of non-specific coloring in the cytoplasm.

Given that a 10-h prestimulation in the presence of anti-TGF-β serum gives a significant increase in the total number of transduced colonies, this prestimulation condition was used in the following experiments. Table 2 details the various types of progenitors which are transduced with this method and the relative effectiveness of expression for each of them. The highest effectiveness of expression is obtained with the most immature progenitors, which are the mixed colonies from CFU-GEMM. These progenitors give colonies containing 1 to $2 \times 10^5$ cells. FIG. 1 shows such a colony. FIG. 2 represents erythroid cells with an expression of the homogeneous nls-lacZ gene in all the cells. FIG. 3 details in a more precise way the nuclear localization of β-galactosidase in the macrophages and proves the absence of non-specific coloring in the cytoplasm. Prestimulation by means of anti-TGF-β increases the transfer effectiveness from 54.5 to 95% in CFU-GEMMs (colony-forming units—granulocyte/erythrocyte/macrophage/megacaryocyte), from 43.8 to 66.2% in BFU-Es (burst-forming units—erythroid), from 3.5 to 13.5% in CFU-GMs (colony-forming units—granulocyte/macrophage), from 0 to 9.3% in CFU-Gs (colony-forming units—granulocyte) and from 8.3 to 22.2% in CFU-Ms (colony-forming units—macrophage). Transfer effectiveness is increased compared with the transfection conditions of CFU-GEMM without TGF-β.

Prestimulation by means of anti-TGF-β increases the stability of the expression of the gene during the development of CFU-GEMMs.

Given that the CFU-GEMMS represent a sub-population of the compartment of the stem cell which takes part in long-term hematopoietic reconstitution (Lu, L., Xiao, M., Shen, R.-N., Grisby, S., & Broxmeyer, H. E. (1993) Blood 81, 41–48), the stability of the expression of the gene during the development of the CFU-GEMMS in mixed colonies was analyzed. In table 3, the CFU-GEMMs are classed according to the percentage of cells expressing nls-lacz, inside each of the colonies. Prestimulation by means of anti-TGF-β serum increases the number of colonies containing from 90 to 100% of cells expressing the nls-lacz gene. This type of CFU-GEMM does not develop in cultures of cells which are not prestimulated by an anti-TGF-β serum. On the contrary, this sub-population represents 41.2% of all the CFU-GEMMS transduced after prestimulation by means of anti-TGF-β serum.

It was determined whether the size of the colonies is changed by the transfer of genes. It is observed that the number of cells is not significantly different in the colonies transduced by means of nla-lacZ compared with those that are not.

TABLE 1

The anti-TGF-β serum added during a 10-h prestimulation increases the effectiveness of gene transfer.

| Hours | Anti-TGF-β antiserum | Total number of colonies | Transfected colonies | % transfer |
|---|---|---|---|---|
| 0 | − | 103(±16) | 1(±0) | 1.1(±.05) |
|  | + | 94(±18) | 2(±2) | 1.54(±.4) |
|  |  | df = 2; | df = 2; | df = 2; |
|  |  | p = 0.330 | p = 0.028 | p = 0.128 |
| 10 | − | 74(±19) | 15(±5) | 23.8(±9.0) |
|  | + | 125(±15) | 51(±10) | 24.8(±2.09) |
|  |  | df = 3; | df = 3; | df = 3; |
|  |  | p = 0.001 | p = 0.0004 | p = 0.034 |
| 20 | − | 110(±7) | 24(±5) | 23.5(±1.66) |
|  | + | 140(±4) | 35(±4) | 24.8(±2.2) |
|  |  | df = 2; | df = 2; | df = 2; |
|  |  | p = 0.015 | p = 0.085 | p = 0.394 |
| 48 | − | 91(±15) | 20(±6) | 21.9(±3.7) |
|  | + | 113(±10) | 21(±4) | 18.7(±2.2) |
|  |  | df = 2; | df = 2; | df = 2; |
|  |  | p = 0.138 | p = 0.440 | p = 0.394 |

The number of colonies is obtained with $10^3$ cells/ml cultivated in methyl cellulose as described in Material and Methods.

TABLE 2

Effect of the anti-TGF-β serum on the effectiveness of transfer into different types of hematopoietic progenitors.

| Progenitors | | % transfer without prestimulation by anti-TGF-β | % transfer with prestimulation with anti-TGF-β |
|---|---|---|---|
| CFU-GEMM | Total number of colonies | 11 | 21 |
| | Transfected colonies | 6 | 20 |
| | % transfer | 54.5 | 95 |
| BFU-E | Total number of colonies | 67 | 83 |
| | Transfected colonies | 19 | 55 |
| | % transfer | 43.8 | 66.2 |
| CFU-GM | Total number of colonies | 28 | 38 |
| | Transfected colonies | 1 | 5 |
| | % transfer | 3.5 | 13.5 |
| CFU-G | Total number of colonies | 21 | 43 |
| | Transfected colonies | 0 | 4 |
| | % transfer | 0 | 9.3 |
| CFU-M | Total number of colonies | 12 | 18 |
| | Transfected colonies | 1 | 4 |
| | % transfer | 8.3 | 22.2 |

CFU-GEMM: colony-forming unit - granulocyte/erythrocyte/macrophage/megacaryocyte;
BFU-E: burst-forming unit - erythroid;
CFU-GM: colony-forming unit - granulocyte/macrophage;
CFU-G: colony-forming unit - granulocyte;
CFU-M: colony-forming unit - macrophage.

This is the result of one experiment among 3 similar experiments.

TABLE 3

Distribution of the transfected CFU-GEMMS according to the stability of the expression of the nls-lacZ gene during the development of the colony.

| % of cells expressing the nls-lacZ gene in each mixed colony | Without anti-TGF-β serum | | With anti-TGF-β serum | |
|---|---|---|---|---|
| | % of mixed colonies | number of cells per mixed colony | % of mixed colonies | number of cells per mixed colony |
| 90–100 | 0 | 118 706 (± 16 300) | 41.2 | 152 776 (± 18 336) |
| 40–90 | 66.6 | 121 766 (± 10 821) | 35.3 | 156 456 (± 19 069) |
| 0–40 | 33.3 | 122 313 (± 13 590) | 23.5 | 169 963 (± 16 919) |

The results represent the average (±SD) of 3 independent experiments.

Table 4. Effect of the anti-TGP-β serum and/or of the anti-interferon (IFN) on the titer of the supernatant produced by the NB16 cell.

| Supernatant | Control | anti-IFN antiserum | anti-TGF-β antiserum |
|---|---|---|---|
| CFU/10$^{-5}$ number of experiments | 6(±4.4) (n = 6) | 65.8 (±68.7) (n = 6) | 38.2 (±42.02) (n = 4) |

NB16 cells were cultivated in the absence or in the presence of anti-TGF-β or of anti-interferon.

The supernatants are then added to the cultures of non-confluent 3T3 cells. When the cells are confluent, they are colored by X-Gal and the viral foci are counted and the titer is expressed by the number of viral foci multiplied by the inverse of the dilution of the initial supernatant.

The addition of anti-TGF-β or of anti-interferon during the coculture can increase the transfer percentage (result not shown) in the hematopoietic cells through a direct effect on the producer line. Table 4 shows in fact that, when anti-TGF-β or a viral agent such as an anti-interferon is added to the NB16 cells, the titer of the supernatant is increased. The supernatant obtained after treatment with anti-interferon actually increases by 11 times the number of infection foci and with anti-TGF-β it increases by 6 times.

EXAMPLE 2

The results obtained in tests comparing prestimulation with or without an anti-inhibitor of the cell cycle are given below.

The purpose of the example is to remove from the quiescent phase primitive progenitors which would be under the control of an autocrine TGF-β. This removal is achieved after a short stimulation period (10 hours) then the phenomenon is demonstrated by placing activated progenitors in a semi-solid culture and reading the number of mixed colonies after 21 days of culture (Faumer A. A. and Messner H. A. (1979), Identification of Megakaryocytes, Macrophages, and Eosinophils in Colonies of Human Bone Marrow Containing Neutrophilic Granulocytes and Erythroblasts. Blood, 53: 1023–1027).

Experimental protocol:

Purification of the CD34+ cells of cord blood.

The cells are incubated in 2 different basic media:

A: GTL medium, and

B: standard liquid medium with 10% fetal calf serum.

The composition of the GTL medium is described in "Specific role of lipids, transferrin and insulin in defined media for cells of the human hematopoietic and immune systems", J. Hatzfeld, A. Hatzfeld, J. Maigné, M. Sasportes, R. Willis and D. B. McClure in Cold Spring Harbor Conferences on Cell Proliferation Vol. 9, Growth of Cells in Hormonally Defined Media, 1982, pp. 703–710.

The composition of the GTL medium is as follows:

IMDM: basic medium,

+ 1 mg/ml reconstituted delipidated bovin serum albumin with 5 μg/ml oleic acid, 5 μg/ml linoleic acid, 1 μg/ml palmitic acid, + transferrin 5 μg/ml ("Specific role of lipide, transferrin and insulin in defined media for cells of the human hematopoietic and immune systems", J. Hatzfeld, A. Hatzfeld, J. Maigné, M. Sasportes, R. Willis and D. B. McClure in Cold Spring Harbor Conferences on Cell Proliferation Vol. 9, Growth of Cells in Hormonally Defined Media, 1982, pp. 703–710).

The composition of the standard medium is as follows: IMDM+10% fetal calf serum, 1 mg/ml bovin serum albumin, 2 mM glutamine, 10 μg/ml transferrin, and $4 \times 10^{-5}$ M β-mercaptoethanol.

At least 6 of the following cytokines are added to these two basic media: IL1, IL2, IL3, IL4, IL5, IL6, IL7, IL11, GCSF, SF, EPO, GM-CSF, FL, TPO, FGF, insulin or synthokins activating the receptors corresponding to these cytokines.

In each group of media A and B, the following conditions are tested:

1) control: nothing else is added, and
2) addition of an anti-TGF-β antibody from Stem GEM* CNRS, 7 rue Guy Môquet, 94801 Villejuif, FRANCE.

The cells are placed in the oven for 10 hours at 37° C., 5% CO2; 1000 cells in 0.4 ml of medium.

At the end of the prestimulation period, 2.1 ml of semi-solid medium are added to the cells. This is incubated for 21 days at 37° C., 5% CO.

Results:

Each figure represents the average of two dishes. Only the counts for mixed colonies (colonies consisting of red cells+ one or more types of lineages of white cells) which come from the most immature cells are counted.

|  | Exp A | Exp B | Exp C |
| --- | --- | --- | --- |
| Control (1) | 8 | 6 | 1 |
| In the presence of anti-TGF-β antibody (2) | 15 | 12 | 4 |

EXAMPLE 3

It was also verified that more elaborate combinations of factors than those already used do not have as efficient an effect as anti-TGF-β.

Numerous combinations, more elaborate than the previous combinations, of cytokines were compared in cultures with and without anti-TGF-β. It was observed that certain combinations of cytokines can have an effect similar to the effect of anti-TGF-β on the colonies which develop rapidly and thus come from already activated slow progenitors. On the other hand, the effect of anti-TGF-β cannot be replaced by any combination of cytokines for the development of colonies over 18 days.

Moreover, although it was known that cytokines induce the amphotropic receptor of the retroviruses used for a transfer of genes, it was shown, thanks to the invention, that anti-TGF-β increases the expression of the receptors of cytokines, and thus their action, and thus the expression of the amphotropic receptors, and thus the transfer of genes. The increase in the expression of the receptors of cytokines for anti-TGF-β is principally clear on quiescent cells.

EXAMPLE 4

A unicellular cultures condition example for (CD34+ CD38 weak cells) compares the effect of FL/bFGF (Flik ligand/basic fibroblast growth factor) and anti-TGF-β-1 antibody (from StemGEM*) in the following medium: medium B: serum/IL3/IL6/SF/GCSF) on D0, and medium B+GMCSF+EPO on D12.

Four culture medium conditions were used:

1. standard medium with 24% fetal calf serum and 4 cytokines (IL3, IL6, SP, GCSF), 2. standard medium with 10% fetal calf serum and 4 cytokines (IL3, IL6, SF, GCSF)+FL/bFGF, 3. standard medium+anti-TGF-β antibody (from Stem GEM*), and 4. standard medium+FL/bFGF+anti-TGF-β antibody (from Stem GEM*), and Results:

The four conditions give the following results:

For the cycling of the cells:
1. 50% of the cells give clones of more than 100 cells,
2. 75% of the cells give clones of more than 100 cells,
3. 75% of the cells give clones of more than 100 cells, and
4. 75% of the cells give clones of more than 100 cells.

There is thus no additive effect in combination 4.

It would appear that it is the same population that is involved.

For proliferation, conditions 2 and 3 give the following results:

Condition 2, 15–20% of the clones contain more than $10^4$ cells,

Condition 3, 50% of the clones contain more than $10^4$ cells.

Thus the anti-TGF-β antibody is more effective than the FL/bFGF.

Regarding the type of cells obtained:

with combination 2, it is principally Gs and Ms (more mature cells) that are obtained, i.e., granulocytes and monocytes.

with combinations 3 and 4, it is principally red and mixed cells (i.e. a mixture of red cells and white cells) that are obtained.

The antibody thus induces the cycling of earlier cells, since it is only with the anti-TGF-β antibody that the erythroid or mixed paths are stimulated.

Overall these results reveal the advantages of the brief treatment by means of anti-TGF-β according to the invention.

All publications dealing with the transfer of genes stress the two important parameters of an effective transfer: a supernatant with a high viral titer and the cycling of the cell to be infected. This is the reason why the stem cells are stimulated with cytokines. In the publications, stimulation takes place for more than 72 hours and concerns cells which are already in cycle. At the end of 72 hours, many of these cells have already started to differentiate. The cells which are infected are thus much less immature than at the start. With anti-TGF-β, and in accordance with the method of the invention, the cells are stimulated for a very short time and are cells which are initially quiescent. They have only had time to enter into cycle, with no or little differentiation. The method of the invention allows them to be returned to the quiescent phase immediately after the transfer of genes thanks to a brief treatment by means of TGF-β. As a result, the cells which are transfected are more immature, which is the end that is sought in gene therapy using hematopoietic stem cells. This method can be applied to other types of cells, possibly using other anti-inhibitors of the cell cycle (anti-Rb: retinoblastoma susceptibility antigen, anti-INK: kinase anti-inhibitor, etc.).

These anti-inhibitors can be antisense oligonucleotides, blocking antibodies, natural or synthetic inhibitors.

What is claimed is:

1. In a method of efficient gene transfer, a method of prestimulation comprising the steps of:
   providing a culture containing primitive stem cells in a quiescent state;
   providing a time-limited prestimulation of said primitive stem cells by adding a blocking means to said culture to block at least one inhibitor of a cell cycle of said primitive stem cells, wherein said time-limited prestimulation is for a period less than approximately 36 hours so that said culture of primitive stem cells retains hematopoietic potential.

2. The method of claim 1, further comprising the steps of:
   after the step of providing a culture of primitive stem cells in a quiescent state, preparing a blocked culture by placing a first portion of said primitive stem cells using a culture medium, and completing the step of providing a time-limited prestimulation with said first portion;
   preparing a non-blocked culture with a second portion of said primitive stem cells in said culture medium, leaving said culture medium free of said blocking means; and
   comparing a degree of maturity of said blocked and non-blocked cultures of said primitive stem cells so that the first portion can be evaluated to determine the presence of quiescent primitive cells.

3. The method of claim 1, further comprising the step of, after the time-limited prestimulation step, transferring genes into said primitive stem cells.

4. The method of claim 1, further comprising the steps of:
   providing primitive stem cells which are hematopoietic cells; and
   providing said block means using anti-TGF-β.

5. The method of claims 1, wherein said blocking means comprises anti-TGF-β from 0.01 µM to 0.5 µM.

6. The method of claim 1, wherein said step of prestimulating stem cells occurs for a period less than approximately 10 hours.

7. Quiescent stem cells containing a heterologous gene in the genome, obtained by the production of hematopoietic stem cells by a method comprising:
   prestimulating stem cells, said stem cells being primitive quiescent hematopoietic stem cells, for a period so that said stem cells remain substantially primitive, said period being less than approximately 36 hours, in a medium comprising blocking means for blocking at least one inhibitor of a cell cycle of said stem cells, to release said stem cells from their quiescent state, and cytokines for permitting at least one of the activation of said cell cycle and the passage of at least one subsequent cell cycle;
   contacting said prestimulated stem cells with a heterologous gene in a transfer medium permitting transfer of said heterologous gene into the genome of said prestimulated stem cells so that said genome contains said heterologous gene; and
   after said contacting step, returning said stem cells to a controlled quiescent state so that said stem cells have been transfected while retaining their differentiation potential.

8. A primitive hematopoietic stem cell comprising a genome with a heterologous gene, wherein said stem cell has a multiplication potential of $1\times10^6$ and a differentiation potential covering all hematopoietic lineages.

9. The stem cell of claim 8, further comprising a blocking inhibitor of its cell cycle located either on a surface of or interior to said stem cell.

10. The stem cell of claim 8, wherein said stem cell is in a controlled quiescent state.

11. The stem cells of claim 7, wherein said blocking means is selected from the group consisting of an agent blocking tumor-suppressing genes, an antisense oligonucleotide of TGF-β, an antibody neutralizing TGF-β, a soluble receptor of TGF-β, a natural inhibitor of TGF-β, a synthetic inhibitor of TGF-β, and an inhibitor of the TGF-β synthesis path.

12. The stem cell of claim 8, wherein said heterologous gene is selected from the group consisting of: marker genes, hematopathy correcting genes, and pathology correcting genes.

13. The stem cell of claim 12, wherein said heterologous gene is selected from the group consisting of: a neomycin resistance gene, a leucocytic antigen, a nls-lacZ gene, a adenosine deaminase gene, a gene correcting adrenoleucodystrophy, and a suicide gene allowing cells to be killed in the presence of acyclovir under the control of viral promoters.

14. A method of transferring a heterologous gene into a primitive cell genome activated from a quiescent state, comprising the steps of:
   prestimulating primitive cells, said cells being in a quiescent state, for a period so that said primitive cells remain substantially primitive, said period being less than approximately 36 hours, in a medium comprising blocking means for at least one inhibitor of a cell cycle of said primitive cells, to release said primitive cells from the quiescent state, and cytokines for permitting at least one of the activation of said cell cycle and the passage of at least one subsequent cell cycle;
   contacting said primitive cells with a heterologous gene in a transfer medium permitting transfer of said heterologous gene into the genome of said primitive cells so that said genome contains said heterologous gene; and recovering said primitive cells obtained in said contacting step.

15. The method of claim 14, wherein in said prestimulation step, said primitive cells are hematopoietic stem cells.

16. The method of claim 15, wherein said contacting step occurs with a coculture of said primitive stem cells and cells producing one of a viral vector and a retrovirus containing the heterologous gene to be transferred.

17. The method of claim 15, wherein said contacting step occurs by bringing together said primitive stem cells and a supernatant of cells containing one of a viral vector and a retrovirus containing the heterologous gene to be transferred.

18. The method of claim 15, wherein said contacting step occurs using one of a viral vector and a retrovirus produced by a producer culture, said producer culture having comprised one of an anti-TGF-β, an anti-interferon, and a vector-stabilizing agent.

19. The method of claim 15, wherein said blocking means is selected from the group consisting of an antisense oligonucleotide of TGF-β, an antibody neutralizing TGF-β, a soluble receptor of TGF-β, a natural inhibitor of TGF-β, and a synthetic inhibitor of TGF-β.

20. The method of claim 19, wherein said prestimulation step occurs for a period less than approximately 10 hours.

21. The method of claim 15, wherein said medium further comprises a four cytokine combination selected from the group consisting of IL1, IL2, IL3, IL4, IL5, IL6, IL7, IL11, GM-CSF, G-CSF, steel factor, ligant of FLT3, erythropoietin, TNF, LIF, thrombopoietin, insulin, and synthetic synthokin.

22. The method of claim 15, wherein said gene to be transferred is contained within a viral vector or a retrovirus and said transfer medium is comprised of IMDM, cytokines, and one of the group consisting of an antagonist of TGF-β, and an anti-interferon so that production of said viral vector or retrovirus is increased.

23. The method of claim 14, wherein upon conclusion of said contacting step, said cells comprise a culture of hematopoietic stem cells suitable for obtaining differentiated blood cells.

24. The method of claim 15, wherein said prestimulation step occurs for a period less than approximately 10 hours and further comprising the step of, prior to said recovery step, returning said cells to a controlled quiescent state using an inhibitor of the cell cycle.

25. A method of increasing the titer of a vector, comprising the steps of:

providing a producer culture, said producer culture including one of an anti-TGF-β and an anti-interferon; and producing a viral vector or a retrovirus by said producer culture.

* * * * *

SEQUENCE LISTING

<160> NUMBER OF SEQ ID NOS: 1

<210> SEQ ID NO 1
<211> LENGTH: 21
<212> TYPE: DNA
<213> ORGANISM: Unknown
<220> FEATURE:
<223> OTHER INFORMATION: Description of Unknown Organism:NONE

<400> SEQUENCE: 1
cccggagggc ggcatggggg a                                                    21